United States Patent
Fleig et al.

(10) Patent No.: US 7,686,509 B2
(45) Date of Patent: Mar. 30, 2010

(54) MEDICAL UPRIGHT POSITIONING DEVICE AND SYSTEM

(75) Inventors: Oliver Fleig, Baldham (DE); Philipp Pousset, Garching (DE)

(73) Assignee: BrainLAB AG, Feldkirchen (DE)

( * ) Notice: Subject to any disclaimer, the term of this patent is extended or adjusted under 35 U.S.C. 154(b) by 352 days.

(21) Appl. No.: 11/754,530

(22) Filed: May 29, 2007

(65) Prior Publication Data

US 2009/0003531 A1    Jan. 1, 2009

Related U.S. Application Data

(60) Provisional application No. 60/822,444, filed on Aug. 15, 2006.

(30) Foreign Application Priority Data

Jun. 7, 2006    (EP)    .................................. 06011730

(51) Int. Cl.
G21K 5/08    (2006.01)
A61B 6/04    (2006.01)
(52) U.S. Cl. ...................................... 378/192; 378/205
(58) Field of Classification Search ................. 378/167, 378/177, 180, 189, 190, 192, 208; 5/604, 5/624; 128/845, 846, 882
See application file for complete search history.

(56) References Cited

U.S. PATENT DOCUMENTS

| 1,642,915 | A | * | 9/1927 | Adrian | 378/192 |
|---|---|---|---|---|---|
| 2,141,857 | A | * | 12/1938 | Gamble | 378/62 |
| 2,146,913 | A | * | 2/1939 | Piotrowski | 378/175 |
| 2,353,969 | A | * | 7/1944 | Powers | 378/177 |
| 2,478,611 | A | * | 8/1949 | Vogeli | 378/175 |
| 2,774,884 | A | * | 12/1956 | Fox | 378/180 |
| 3,256,611 | A |   | 6/1966 | Deming |  |
| 3,521,876 | A | * | 7/1970 | Smith | 5/601 |
| 3,524,057 | A | * | 8/1970 | Hammonds | 378/174 |
| 3,700,894 | A |   | 10/1972 | Counsell |  |
| 4,320,749 | A | * | 3/1982 | Highley | 602/27 |
| 4,694,478 | A | * | 9/1987 | Delnon | 378/39 |
| 5,479,471 | A | * | 12/1995 | Buckland | 378/208 |
| 5,790,998 | A | * | 8/1998 | Crescimbeni | 5/648 |
| 5,944,676 | A | * | 8/1999 | Grassi | 602/23 |
| 6,969,193 | B1 | * | 11/2005 | Pigg | 378/180 |

* cited by examiner

*Primary Examiner*—Edward J Glick
*Assistant Examiner*—Anastasia Midkiff
(74) *Attorney, Agent, or Firm*—Renner, Otto, Boisselle & Sklar, LLP

(57) ABSTRACT

A medical upright positioning device includes a planar structure having a foot positioning device. At least one outer edge of the planar structure comprises an abutting or engaging device arranged in a predefined positional relationship to the foot positioning device, wherein the abutting or engaging device is operative to position the planar structure in at least one predefined orientation relative to a reference direction.

19 Claims, 3 Drawing Sheets

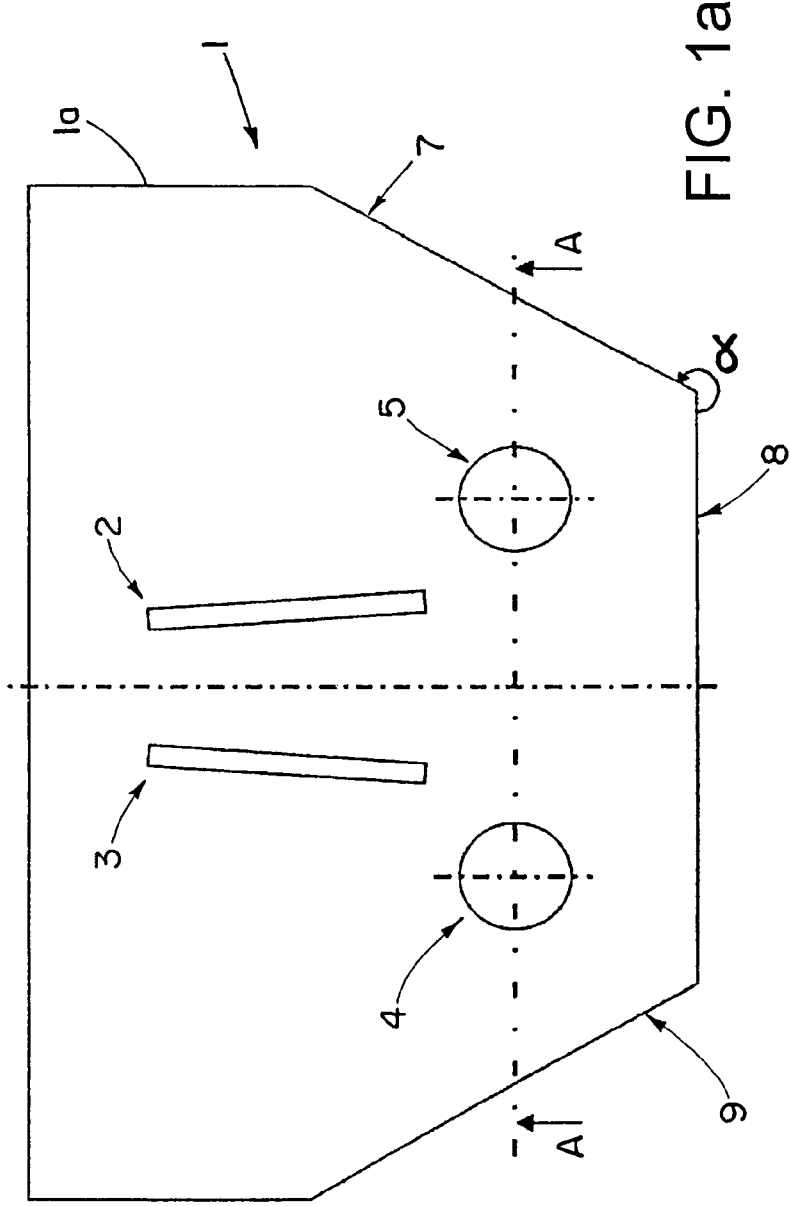
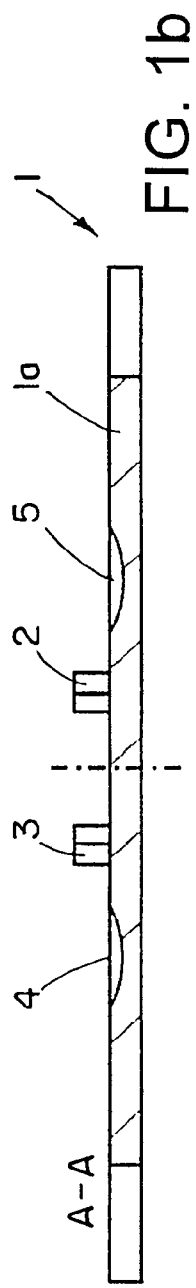

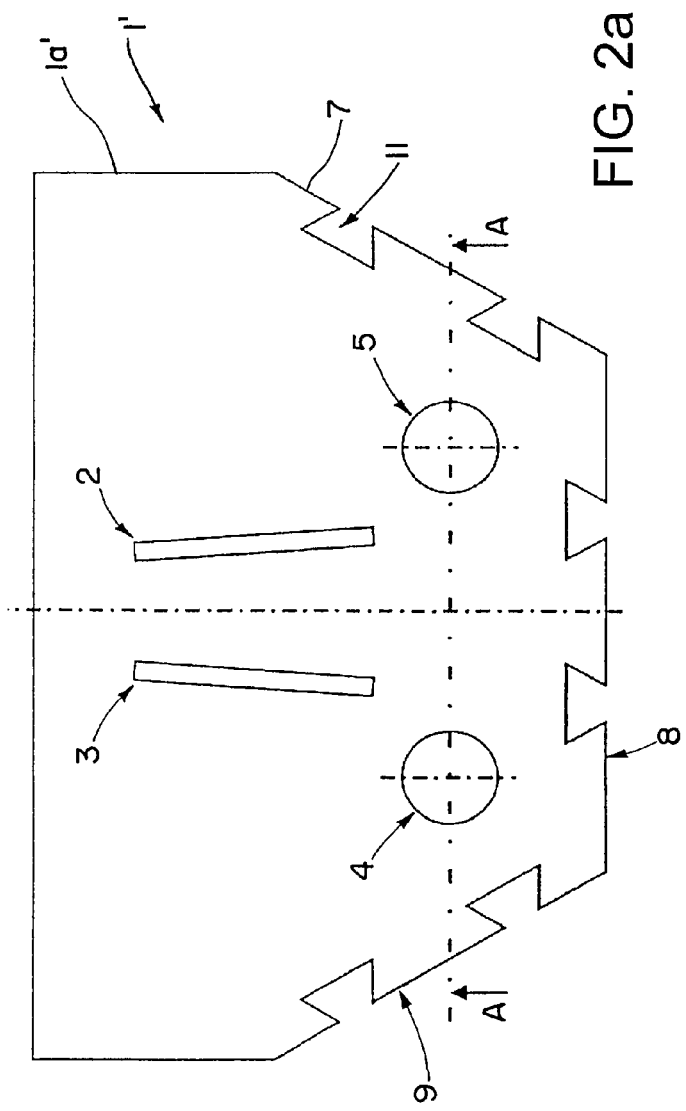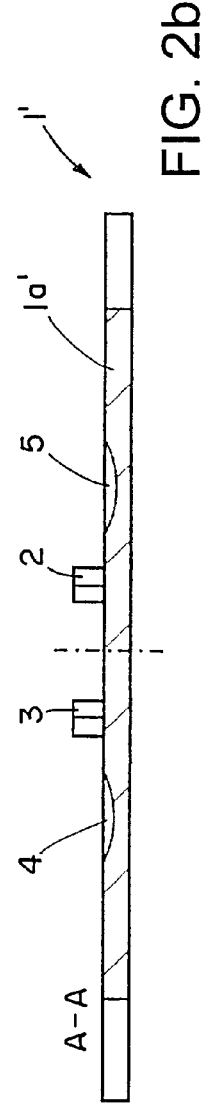

MEDICAL UPRIGHT POSITIONING DEVICE AND SYSTEM

RELATED APPLICATION DATA

This application claims priority of U.S. Provisional Application No. 60/822,444 filed on Aug. 15, 2006, which is incorporated herein by reference in its entirety.

FIELD OF THE INVENTION

The invention relates generally to medical imaging and, more particularly, to a medical upright positioning device and a medical upright positioning system.

BACKGROUND OF THE INVENTION

Medical upright positioning devices may be used to record x-ray images of a standing patient in predetermined positions. For some applications, it may be necessary to obtain image data from multiple angles (e.g., for the hip area) for later evaluation (e.g., on a computer screen). In standardized evaluation methods, it is possible to roughly plan the treatment in advance with the aid of such image information, e.g., to roughly plan the placement of implants into the image data, wherein implant data may be stored in a computer system.

In order to perform such advance planning steps, however, it should be ensured that during recording, the patient is precisely situated in a desired recording direction, e.g., a first recording directly from the front (anterior-posterior) and a second recording at an angle of 60° to the x-ray film.

Various attempts have been made to achieve said predetermined patient positionings. For example, foils or templates indicating multiple foot positions have been placed on the floor in front of the x-ray film. The patient then may be instructed to position himself on the foot depictions in accordance with the desired position. A disadvantage of such foils or templates is that they are easily moved and therefore have to be re-orientated each time they are used, e.g., by way of a line marked on the floor. If they are not properly re-orientated, the patient position in the x-ray image may be incorrect.

Another approach is to attach to the patient a calibration object that can be depicted in the images. The technique used in this case can be elaborate, and it is possible that the calibration object may move relative to the patient while he is being repositioned. This can lead to imprecise position determinations.

A patient positioning device is known, for example, from U.S. Pat. No. 3,700,894, which comprises foot stoppers attached to rotating bars, and head mounts. The device, however, is in turn configured very elaborately and must permanently remain at its location.

SUMMARY OF THE INVENTION

A medical upright positioning device includes a foot attachment planar structure comprising foot positioning means. The outer edges of the foot attachment planar structure may have abutting or engaging means that are in a predefined positional relationship to the foot positioning means.

In other words, the upright positioning device is formed such that its outer circumference or sides can serve as an orientation aid for the device as a whole. The device thus includes information for the patient that shows him where he is to position his feet, and the orientation aid for the device itself, e.g., on the outer circumference or sides of the foot attachment planar structure. Since the outer edges comprise stoppers or engagements, it is possible to ensure in a very simple way that the device is correctly orientated and, therefore, that the patient is also correctly orientated.

As compared to methods that use calibration objects, the positioning device described herein has the advantage that image processing errors that may arise due to calibration objects shifting do not occur. Further, the need to perform corresponding image processing can be eliminated. Because the device is uncomplicated and can be provided with few components, it rises above complicated, technically elaborate devices that permanently remain at the examination location (e.g., as described in U.S. Pat. No. 3,700,894). The construction of the device can implicitly define the angular orientation of the foot positioning means, such that an incorrect angle cannot be selected. Since the outer edges of the device define its orientation, it merely need be placed onto an appropriately orientated counter or reference element, for example onto the wall on which the x-ray film holder is also arranged. Its use is self-explanatory and no additional adjustments are required. The upright positioning device can be provided in an embodiment that is easy to construct and has easy-to-handle dimensions. Installation of the positioning device is not complicated, and once used, it can be easily removed from the working area and stowed in a space-saving way.

The positioning device may include multiple abutting or engaging means, in particular at least two, and can be in different predefined positional relationships relative to the foot positioning means, in particular in different angular arrangements in relation to the foot positioning means.

The foot attachment planar structure can include a rigid plate, and the abutting or engaging means can be formed by the outer edges of the plate or can be provided on the outer edges. It is also possible for the abutting or engaging means to be formed by at least two outer edges that are arranged at a predefined angle to each other, in particular at an external angle of 200 degrees to 280 degrees, specifically at an external angle of 240 degrees. In the latter case, the patient could then be rotated by 60 degrees between two recordings if the device is used by positioning on two different outer edges.

The outer edges can assume different embodiments. They can be linear, continuous abutting edges or can comprise coupling engagements, in particular coupling protrusions and/or coupling grooves along at least a part of their length. Another possible embodiment is to arrange undercut cavities on the outer edges. Undercut protrusions also can be arranged, depending on the shape of the counter or reference element for positioning the device.

Other embodiments relate to the foot positioning means. The foot positioning means can comprise, for example, a heel cavity for at least one foot and in particular only one lateral positioning foot stopper per foot. Such a heel cavity ensures that the patient's foot will not slip, and a single lateral, for example medial, foot stopper is sufficient for establishing a defined foot orientation.

The foot stopper can then comprise an abutting edge that protrudes upwards from the foot attachment planar structure.

In accordance with another aspect of the invention, there is provided a system that includes a medical upright positioning device such as described herein, and a positioning counter or reference element that comprises an abutting or engaging means that is complementary to the abutting or engaging means of the upright positioning device. The upright positioning device, for example, can be placed against a wall using one of its edges, and the foot positioning means would immediately be standing in the desired position. In some applications, however, it could be advantageous to provide a counter element (e.g., if the x-ray film holder is not directly attached to a wall). Due to the simple nature of the upright positioning device, a counter element can be provided that comprises, for example, a linear, continuous abutting edge, coupling engagements, in particular coupling protrusions and/or coupling grooves along at least a part of its length, undercut protrusions or undercut cavities and/or a combination of such devices. The system may include floor fastening means or wall fastening means for positioning counter element, in particular friction means, adhesion means, locking means or mechanical fixing means such as screw fasteners. It is also possible to use detachable fastening means to enable removal of the counter element once it has been used and stow, as with the upright positioning device. Examples include fastening means such as suction cups, hook and loop fastenings or detachable adhesive layers.

BRIEF DESCRIPTION OF THE DRAWINGS

The forgoing and other features of the invention are hereinafter discussed with reference to the drawing.

FIG. 1a is a top view of an exemplary upright positioning device in accordance with the invention.

FIG. 1b is a sectional view of the positioning device of FIG. 1a along section A-A.

FIGS. 2a and 2b illustrates exemplary undercut cavities on the positioning edges of the fixing device shown in FIGS. 1a and 1b.

DETAILED DESCRIPTION

Figure 3A:
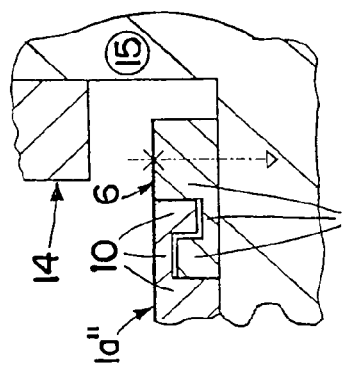
FIGS. 3a and 3b illustrate an exemplary positioning system exhibiting a type of groove-spring edge positioning in accordance with the invention.

FIG. 1a shows an exemplary upright positioning device 1, and FIG. 1b shows a sectional view of the positioning device at the section A-A. The positioning device 1 includes a plate 1a that exhibits a thickness sufficient to form circular recesses 4 and 5 on a top surface of the plate 1a. Each recess 4 and 5 can accept a heel of a patient. Preferably, the plate 1a is at least 1 cm thick, and can be up to 3 to 5 cm thick. With respect to the material, it should be borne in mind that the plate 1a should be easy-to-handle. Therefore, it is preferable that the plate be formed from a relatively light weight material, such as wood or plastic, for example. The plate 1a also includes two medial foot stoppers 2 and 3. A patient can place each heel into a respective recess 4 or 5 and then position the inner side of each foot against the respective foot stoppers 2 and 3. Following this procedure, the patient is standing in a defined and reproducible position.

The plate has an outer circumference or region formed by the outer edges 7, 8 and 9. In the present case, the edges 7, 8, and 9 are abutting edges, i.e., the plate 1a is positioned, for example abutting a wall, using these edges. If the edge 8 of the plate 1a is positioned abutting a wall to which an x-ray film carrier is attached, the patient will stand exactly parallel to the wall, and an anterior-posterior recording can be produced. The two edges 7 and 9 are in precisely defined angular relationships to the edge 8, and FIG. 1a, for example, indicates the angle α, an external angle of 240 degrees. If, after the first anterior-posterior recording, the plate is rotated and for example placed on the same wall using the edge 7 as described above, a recording can be taken in which the patient is recorded obliquely from the front, rotated by 60 degrees.

Using the positioning device 1, it is thus simple to produce x-ray recordings with the patient in exactly defined positions, by simply placing the plate 1a against the wall using different edges. Afterwards, the plate 1a can be stowed and thus does not take up space in the treatment area.

Figure 4A:
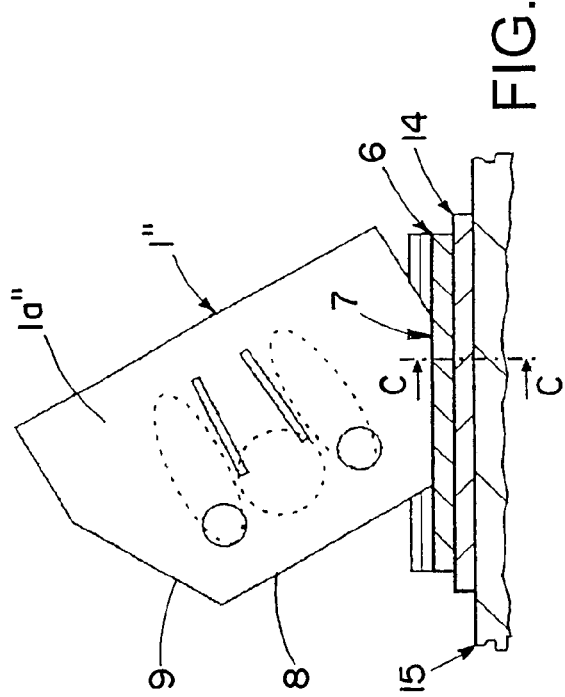
FIGS. 4a and 4b illustrate an exemplary positioning system including a jigsaw-like connection between the upright positioning device and the positioning counter element in accordance with the invention.

FIG. 2 illustrates another exemplary positioning device 1' that includes a plate 1a'. As opposed to the smooth, linear abutting edges of the position device 1 of FIG. 1, the plate 1a' in FIG. 2 comprises cavities 11 on the edges 7, 8, and 9. These cavities expand from the edge in the shape of a trapezium and thus form undercuts, which can be used to precisely anchor the plate 1a' to a positioning counter or reference structure. In order to explain this in more detail, reference will now be made to FIGS. 4a and 4b, which show a plate 1a' in accordance with FIG. 2 and a positioning counter element 6. In the present example, the counter element 6 is a bar that is fastened into the floor (e.g., via screw fasteners or the like), and comprises protrusions 13 that protrude forward and expand in the shape of a trapezium. The protrusions 13 fit into the cavities 11; these two elements are complementary. If, as shown in FIG. 4a, the plate 1a' comprising the cavities 11 is then placed onto the protrusions 13 at the edge 8, such that they are inserted into the cavities 11, the plate 1a' is immovably positioned by the counter element 6, exactly at the angle at which an x-ray recording is to be taken. This of course also applies to the other edges comprising cavities 11, when other angles are to be selected.

Figure 4B:
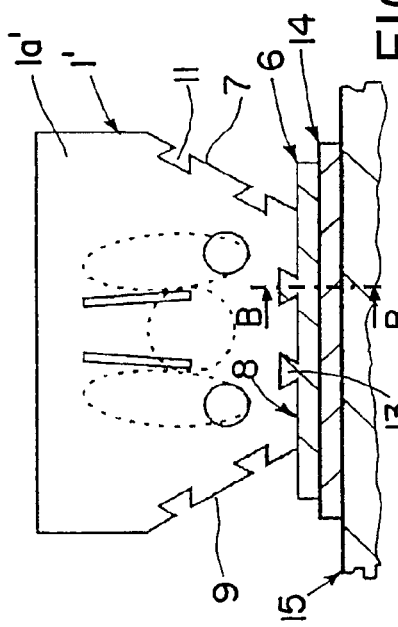

FIG. 4b, which is a section at the plane indicated by B-B in FIG. 4a, also shows that the counter element 6 may be arranged roughly below the x-ray film holder 14 in the area of the wall 15.

Figure 3B:
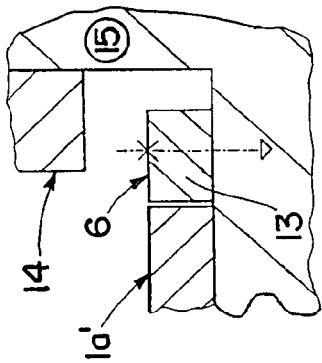

Another type of positioning device 1" comprising a positioning plate 1a" is shown in FIGS. 3a and 3b, wherein FIG. 3B shows a section at the plane indicated by C-C in FIG. 3a. The outer edges 7, 8 and 9 of the plate 1a" in FIG. 3a comprise a coupling groove 10 that opens in a downward direction of a bottom peripheral area. A complementary groove 12 that opens in an upward direction is attached to the counter element 6. The peripheral area 10 of the plate 1a" from FIG. 3a can be hooked or otherwise coupled into the peripheral area 12 of the counter element 6. The plate 1a" then may be arranged on a rail in its respective position, in order to provide the envisaged and predefined angular positions for the patient by using the outer edges 7, 8 or 9. Here, too, FIG. 3b again shows the overall positional relationship between the plate 1a", the counter element 6 and the wall 15 comprising the x-ray film holder 14.

An upright positioning device, even in the system with the counter element, can of course also assume various other embodiments; the jigsaw-like cavities and protrusions 11 and 12 can for example be replaced by other appropriate variants, among other things by cavities and protrusions that do not exhibit an undercut. Also, for example together with the plate 1a, 1a', and/or 1a", an additional spacing element (not shown) could be provided that simply has the shape of a flat beam. This can be used to position the plate according to FIG. 1 correspondingly further from a wall but still exactly in terms of its angle. Such spacing pieces also could be provided with cavities and recesses and/or with coupling devices, in order to then fit embodiments in accordance with FIGS. 2 or 4a and/or 4b.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A medical upright positioning device, comprising a planar structure having a top surface with a foot positioning device, a bottom surface, and at least two outer sides arranged between the top surface and the bottom surface, the at least two outer sides including an engagement device defining first and second abutment planes, respectively, that do not form a right angle and are not parallel to one another, the first and second abutment planes, arranged in a predefined positional relationship relative to the foot positioning device.

2. The upright positioning device according to claim 1, wherein each of the first and second abutment planes are arranged in different predefined positional relationships to the foot positioning device.

3. The upright position device according to claim 2, wherein the different predefined positional relationships include different angular arrangements in relation to the foot positioning device.

4. The upright positioning device according to claim 1, wherein the planar structure comprises a rigid plate.

5. The upright positioning device of claim 1, wherein the first and second abutment planes are arranged at an external angle between 200 degrees and 280 degrees relative to one another.

6. The upright positioning device according to claim 1, wherein at least one of the at least two outer sides defines a linear, continuous abutment plane.

7. The upright positioning device according to claim 1, wherein the engagement device on at least one of the at least two outer sides comprises coupling engagements along at least a part of the outer side.

8. The upright positioning device according to claim 7, wherein the coupling engagements are protrusions and/or grooves.

9. The upright positioning device according to claim 1, wherein the engagement device includes undercut cavities or protrusions arranged on at least one of the at least two outer sides.

10. The upright positioning device according to claim 1, wherein the foot positioning device comprises a heel cavity for at least one heel of a foot and a lateral positioning foot stopper corresponding to the heel cavity.

11. The upright positioning device according to claim 10, wherein the foot stopper comprises an abutting edge that protrudes upward from the planar structure.

12. A system comprising a medical upright positioning device according to claim 1, and a positioning counter element comprising an abutting or engaging device that is complementary to the engagement device of the upright positioning device.

13. The system according to claim 12, wherein the positioning counter element comprises at least one of:
a linear, continuous abutting edge;
coupling engagements; or
undercut protrusions or undercut cavities.

14. The system according to claim 13, wherein the coupling engagements comprise protrusions and/or grooves.

15. The system according to claim 12, further comprising a fastening device for attaching the positioning counter element to a floor or support structure.

16. The system according to claim 15, wherein the fastening device is a friction element, adhesion element, locking element or mechanical fixing element.

17. The system of claim 16, wherein the mechanical fixing element comprises screw fasteners.

18. A medical upright positioning device, comprising:
a planar structure including a foot positioning device, the planar structure having a top surface, a bottom surface, and at least one outer side formed between the top surface and the bottom surface;
a first locking element arranged on a first outer side of the at least one outer side at a first predefined location relative to the foot positioning device, said first locking element configured to inhibit movement of the planar structure;
a second locking element arranged on one of the first outer side or a second outer side of the at least one outer side at a second predefined location relative to the foot positioning device and different from the first predefined location, said second locking element configured to inhibit movement of the planar structure.

19. The medical upright positioning device according to claim 18, further comprising a positioning counter element comprising an abutting or engaging device that is complementary to the first and second locking elements of the upright positioning device.

* * * * *